(12) United States Patent
Sholev

(10) Patent No.: US 8,702,590 B2
(45) Date of Patent: Apr. 22, 2014

(54) SYSTEM FOR POSITIONING ENDOSCOPE AND SURGICAL INSTRUMENTS

(75) Inventor: Mordehai Sholev, Amikam (IL)

(73) Assignee: M.S.T. Medical Surgery Technologies Ltd, Raanana (IL)

( * ) Notice: Subject to any disclaimer, the term of this patent is extended or adjusted under 35 U.S.C. 154(b) by 800 days.

(21) Appl. No.: 12/667,420

(22) PCT Filed: Jul. 1, 2008

(86) PCT No.: PCT/IL2008/000902
§ 371 (c)(1),
(2), (4) Date: Dec. 31, 2009

(87) PCT Pub. No.: WO2009/004616
PCT Pub. Date: Jan. 8, 2009

(65) Prior Publication Data
US 2010/0185212 A1 Jul. 22, 2010

Related U.S. Application Data

(60) Provisional application No. 60/929,528, filed on Jul. 2, 2007.

(51) Int. Cl.
*A61B 1/00* (2006.01)
*A61B 17/00* (2006.01)

(52) U.S. Cl.
USPC ............... 600/102; 600/109; 606/1; 606/130

(58) Field of Classification Search
USPC ......... 600/101–105, 109–112, 131; 606/1, 13
See application file for complete search history.

(56) References Cited

U.S. PATENT DOCUMENTS

| 5,876,325 | A | * | 3/1999 | Mizuno et al. ................. 600/102 |
| 5,971,976 | A | * | 10/1999 | Wang et al. ....................... 606/1 |
| 6,368,332 | B1 | * | 4/2002 | Salcudean et al. ............. 606/130 |
| 6,786,896 | B1 | | 9/2004 | Madhani et al. |
| 8,170,717 | B2 | * | 5/2012 | Sutherland et al. ........... 700/245 |
| 8,256,319 | B2 | * | 9/2012 | Cooper et al. ............. 74/490.01 |

FOREIGN PATENT DOCUMENTS

WO    WO2006/111966    10/2006

* cited by examiner

*Primary Examiner* — Ahmed Farah
(74) *Attorney, Agent, or Firm* — The Law Office of Michael E. Kondoudis

(57) ABSTRACT

The present invention discloses a system for handling a surgical instrument, useful for observation and/or intervention with respect to a patient's body. The system comprising a fixed support; hinge which enable changing of the inclination of the system; actuators system that produce the rotation movement utilized by handling surgical instrument mechanism; a flexible power transmission system; gear housing adapted to change the direction of the motors rotation transmitted by the flexible power transmission system; and, handling surgical instrument mechanism, said mechanism comprising: a first small size moveable element, connected to the gear housing is adapted to simultaneous maneuver of a second moveable element to the four main directions, and/or any other maneuver, e.g., right and left, forward and backward; and, a second moveable element that which is adapted to move the surgical instrument to another directions, zoom in and zoom out, simultaneously rotate the surgical instrument, either clockwise or counter-clockwise, simultaneously rotate the camera housing in respect to the surgical instrument clockwise and counter-clockwise.

17 Claims, 21 Drawing Sheets

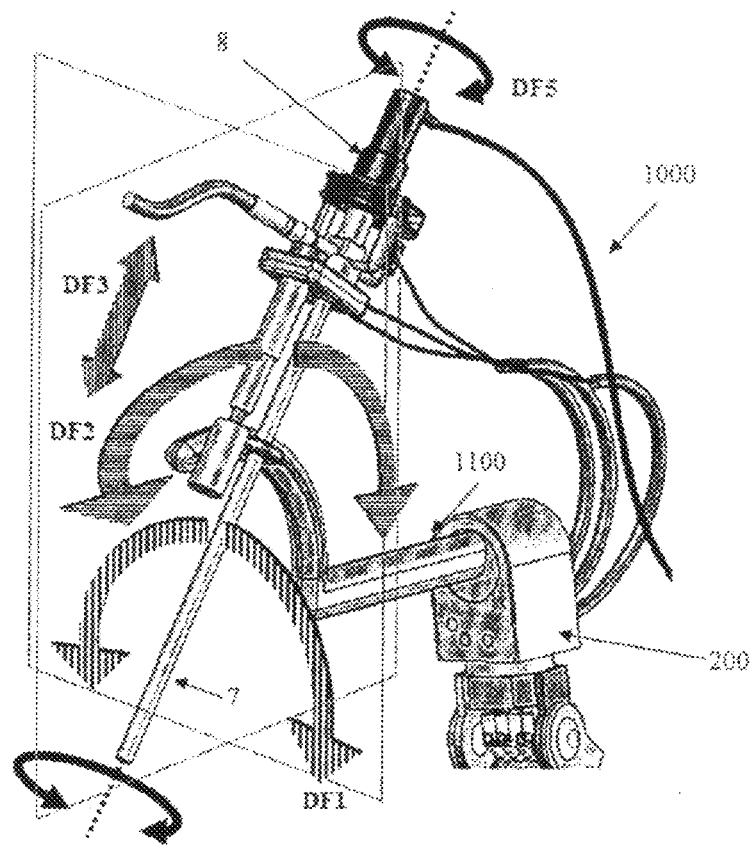
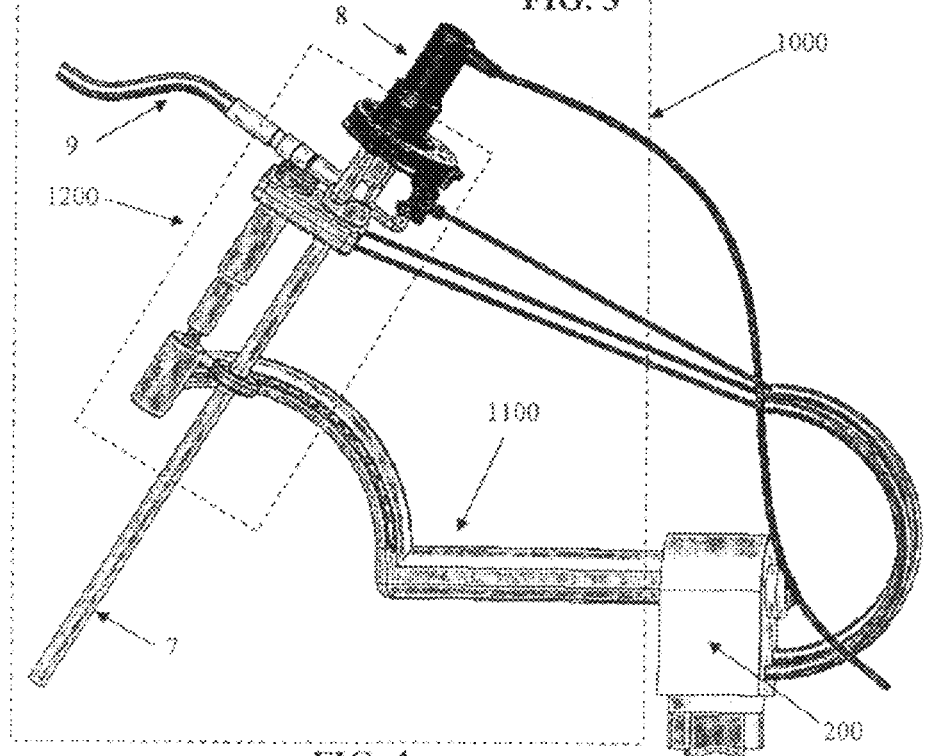
FIG. 3
FIG. 4

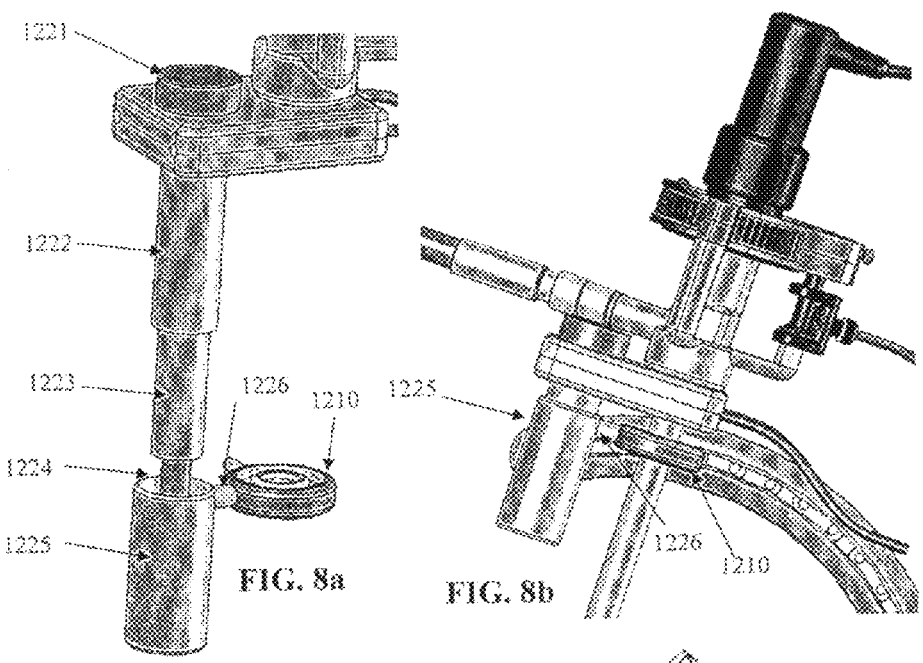
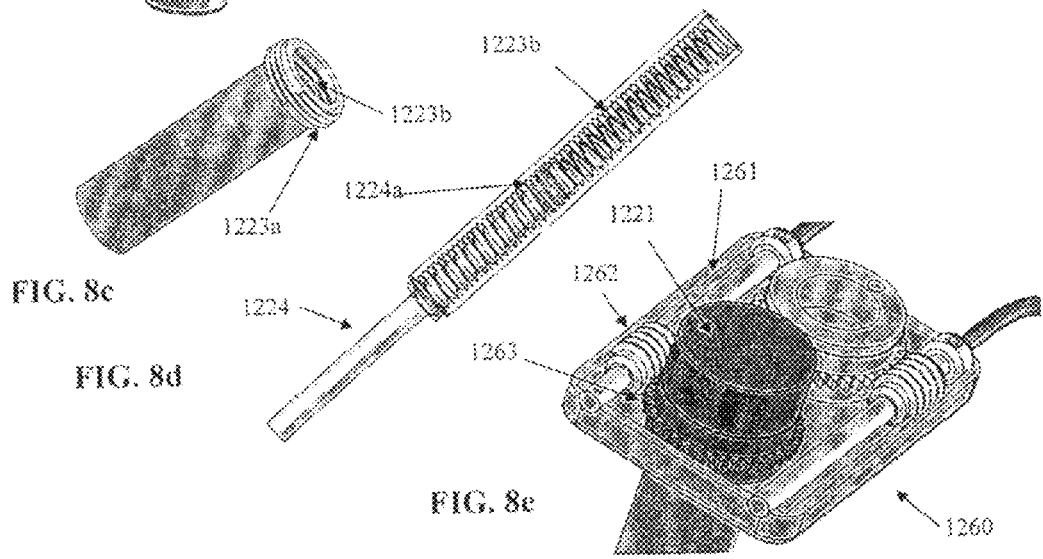
FIG. 8a  FIG. 8b
FIG. 8c
FIG. 8d
FIG. 8e

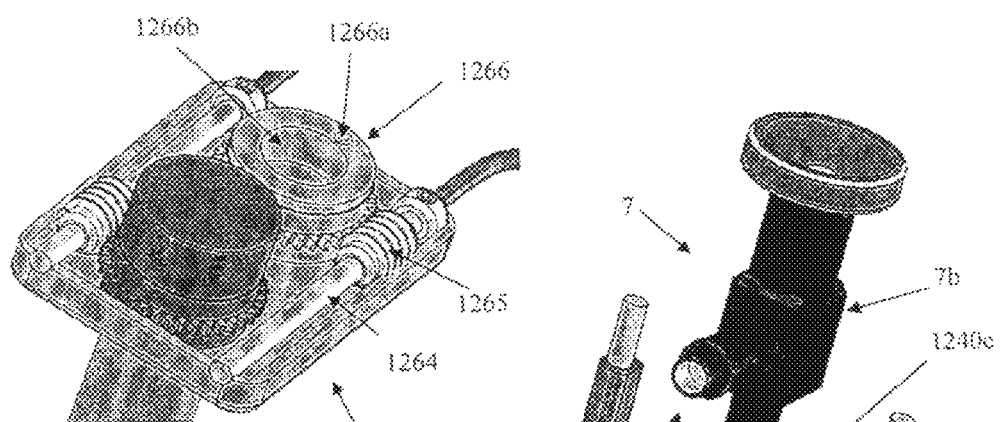
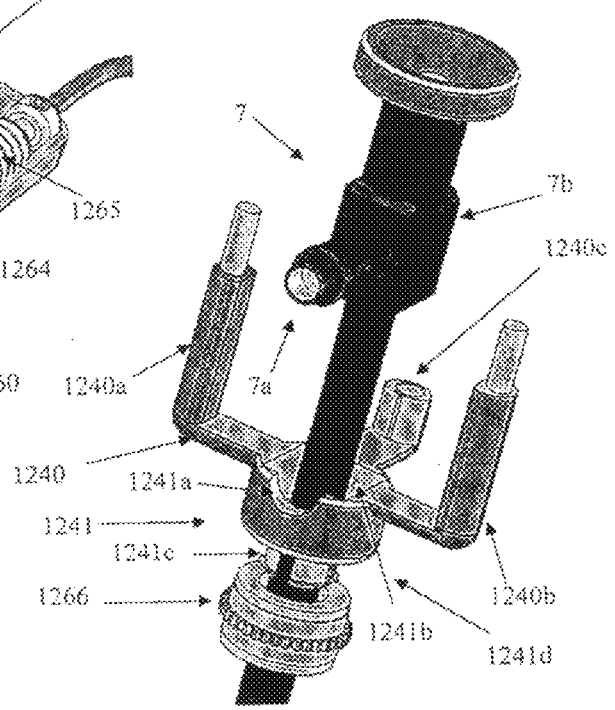
FIG. 9a
FIG. 9b

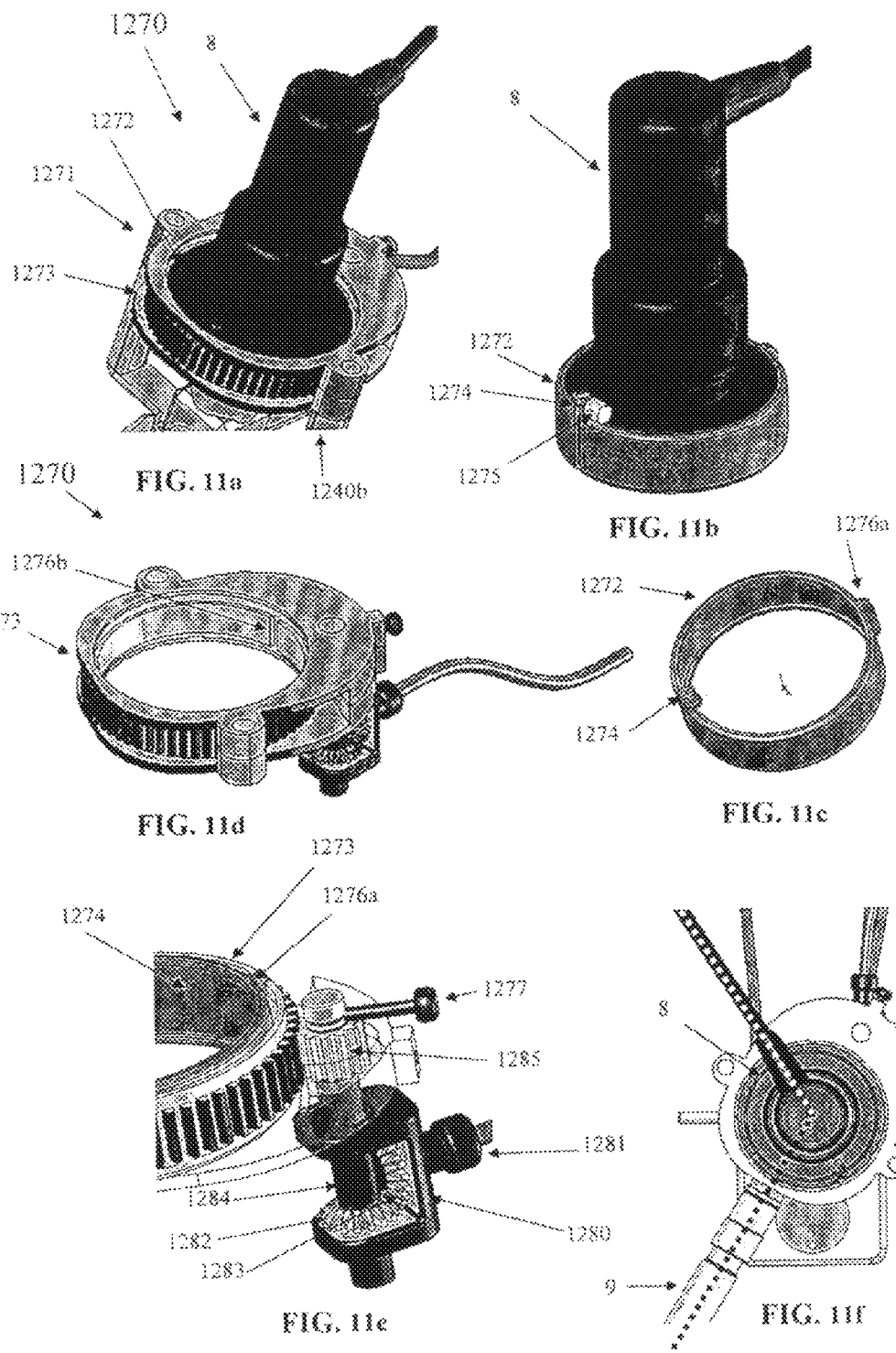

US 8,702,590 B2

SYSTEM FOR POSITIONING ENDOSCOPE AND SURGICAL INSTRUMENTS

CROSS-REFERENCE TO RELATED APPLICATIONS

This application is a National Stage of International Application No. PCT/IL2008/000902, filed Jul. 1, 2008, which claims the benefit of priority of U.S. Provisional Patent Application No. 60/929,528, filed 2 Jul. 2007.

FIELD OF THE INVENTION

The present invention generally relates to means and method of manipulating an endoscope system for laparoscopic surgery, in which the endoscope is inserted through a small incision into the patient body's cavities.

BACKGROUND OF THE INVENTION

In laparoscopic surgery, the surgeon performs the operation through small holes using long instruments and observing the internal anatomy with an endoscope camera. The endoscope is conventionally held by a camera assistant since the surgeon must perform the operation using both hands.

The surgeon performance is largely dependent on the camera position relative to the instruments and on a stable image shown at the monitor.

The main problem is the difficulty for the assistant to hold the endoscope steadily, keeping the scene upright To overcome these problems, several new technologies have been developed, also using robotics to hold the endoscope while the surgeon performs the procedure. Most known of them are Lapman™, EndoAssist™, and Aesop™.

But these technologies are expensive, difficulty installed, uncomfortable to use, limiting the dexterity of the surgeon and having physical dimension much bigger that all operating tools.

Relatively to the required action, they also move in big bounds with several arms movement. The patents of these products are presented in FIGS. 23a, 23b, and 23c.

SUMMARY OF THE INVENTION

It is therefore one object of the present invention to present a novel system for handling a surgical instrument, useful for observation and/or intervention with respect to a patient's body; said system comprising a fixed support; hinge which enable changing of the inclination of the system; actuators system that produce the rotation movement utilized by handling surgical instrument mechanism; a flexible power transmission system; gear housing adapted to change the direction of the motors rotation transmitted by the flexible power transmission system; and, handling surgical instrument mechanism, said mechanism comprising: a first small size moveable element, connected to the gear housing is adapted to simultaneous maneuver of a second moveable element to the four main directions, and/or any other maneuver, e.g., right and left, forward and backward; and, a second moveable element that which is adapted to move the surgical instrument to another directions, zoom in and zoom out, simultaneously rotate the surgical instrument, either clockwise or counter-clockwise, simultaneously rotate the camera housing in respect to the surgical instrument clockwise and counter-clockwise.

The flexible power transmission system is possibly comprised of a plurality of tubes interconnected via a plurality of joints, adapted to rotate to and to keep any desired angle. The tubes possibly contain shafts that transmit the actuators rotation to said gear housing. The gear housing possibly comprises of a plurality of gear transmissions that may move simultaneous the moveable parts of the handling surgical instrument mechanism. The power transmission to the second moveable part of handling surgical instrument mechanism is possibly transferred via flexible means. The gears transmission possibly transfers the power to moveable parts of said first said second moveable element via clutches that stops said power transmission at a desired threshold. The clutches possibly allows the surgeon to move the surgical instrument by without the need to disconnect the surgical instrument from the handling surgical instrument. The first small size moveable element is possibly having a spatial structure, wherein the element contains a pushing and pulling mechanism to produce the forward backward movement of the surgical instrument. The first small size moveable element is possibly connected to a gear transmission of the gear housing that rotates the first moveable element in the right and left directions. The first small size moveable element is possibly having a gimbals' connection to the surgical instrument, insulating the patient body from the handling surgical instrument mechanism. The second small size moveable element is possibly having a linear connection to first small size moveable element. The second small size moveable element is possibly having a gear housing allowing the transfer of the rotation power supplied by said flexible means to produce movements of the surgical instrument in desired directions. The second small size moveable element is possibly having a gear housing allowing the transfer of the rotation power supplied by the flexible means to produce a linear movement of the surgical instrument. The second small size moveable element is possibly having a gear housing allowing the transfer of the rotation power supplied by the flexible means to produce rotation movement of the surgical instrument. The second small size moveable element is possibly having a gear housing allowing the transfer of the rotation power supplied by the flexible means to produce rotation movement of the camera with respect to the surgical instrument. The second small size moveable element is possibly having a quick release mechanism enabling fast removal and fast installation of the surgical instrument. The second small size moveable element is possibly having an adopter allowing using various of surgical instruments. The system is possibly having a structure that has small presence above and near the patient body without distracting the surgeon activities. The handling surgical instrument mechanism is possibly having a structure and mechanism that may be manufactured from inexpensive materials. A disposable handling surgical instrument mechanism is also disclosed.

BRIEF DESCRIPTION OF THE DRAWINGS

FIG. 3 presents the 5 degrees of freedom of the robotic arm;

FIG. 4 shows the robotic arm locked in robotic mechanism housing;

FIG. 8a shows the zoom mechanism and parts;

FIG. 8b shows the zoom in almost its lowest position;

FIG. 8c the screw as a outer thread;

FIG. 8d shows part of the zoom mechanism;

FIG. 8e shows the worm gear that transmits the rotation to the screws of the gear mechanism;

FIGS. 9a and 9b show the mechanism that rotates endoscope;

FIG. 9b shows the endoscope housing;

FIG. 11a to FIG. 11f shows the mechanism that moves the camera head;

DETAILED DESCRIPTION OF THE EMBODIMENTS

The present invention discloses inter alia means for controlling the spatial position of endoscope tube in laparoscopic surgery. The present device is cheap, easily install and disassemble, comfortable to use, not limiting the dexterity of the surgeon and having small physical dimension.

The small size of present invention is achieved by:
1. the shape of the main arm;
2. separating the moving parts from the motors and transmitting the motor power by shafts and cable means;
3. a linear zoom mechanism, allowing a full range zoom action, independent of other moving parts in the mechanism;
4. a rotational mechanism that rotates the endoscope about it's long axis, independently of other moving parts of the mechanism;
5. another rotational mechanism that rotates the digital camera attached to the endoscope about it's long axis, independently of the endoscope and other moving parts of the mechanism The inexpensive price of the present invention is achieved by
1. the small physical dimension of the present invention;
2. the simplicity of the mechanisms of the present invention;
3. the material that may be used to produce the body and the mechanisms of the present invention.

The easy installation and disassemble processes is achieved by 1. the small physical dimension of the present invention;
2. the safety mechanisms of the present invention;
3. the movement compensation mechanisms of the present invention;
4. the separation between the moving parts that are near patient's body from the relatively motors box that is located away from the patient, under the operating table;
5. the flexible structure of the power transmission system that connects the motors box to the moving parts.

Figures 1, 2:
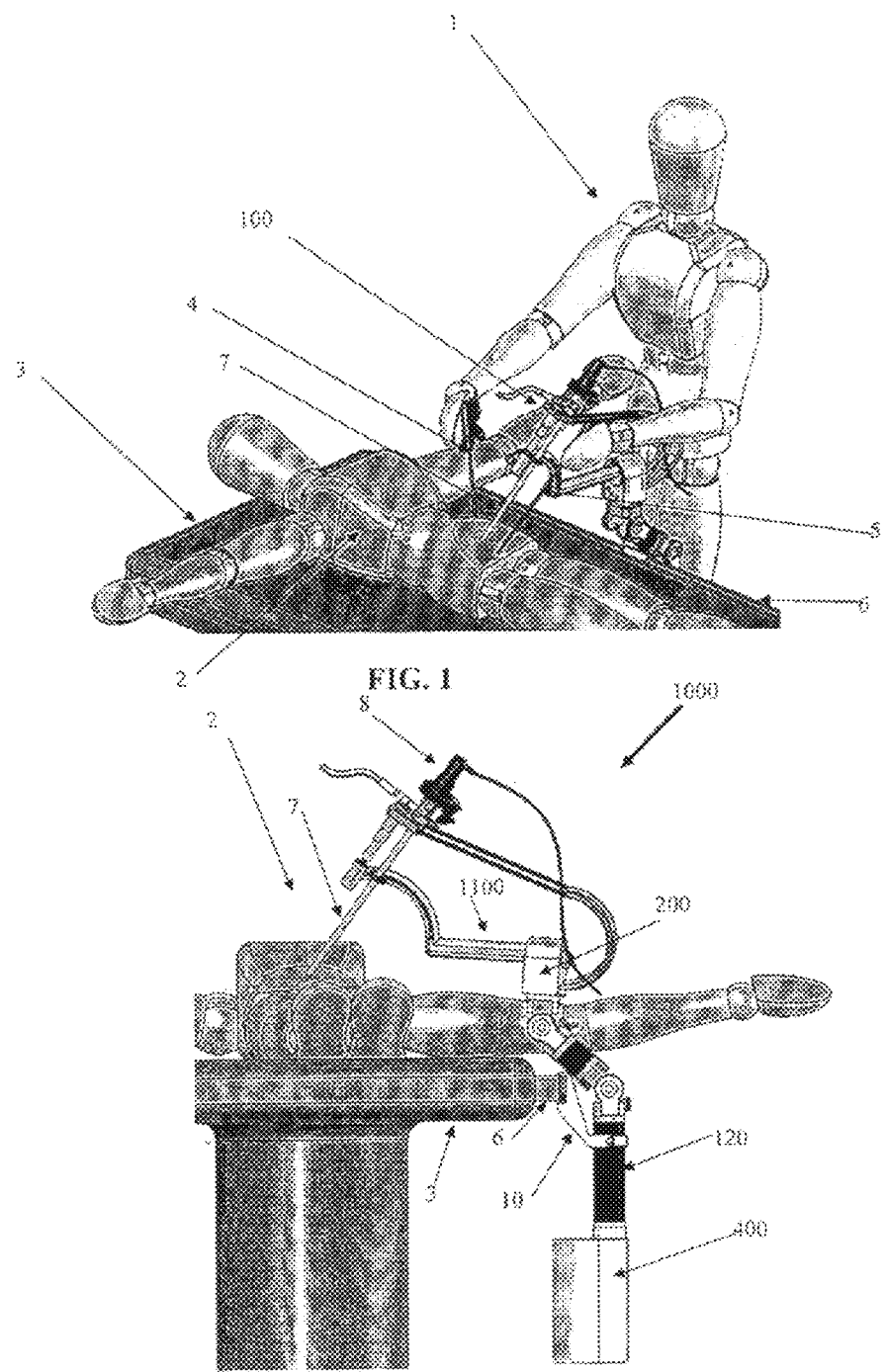
FIG. 1 shows the use of the use of the present invention while performing a laparoscopic procedure in the operating room.
FIG. 2 shows the robotic camera holder attached to the operating table.

FIG. 1 shows the use of the present invention while performing a laparoscopic procedure in the operating room. The patient 2 is laid on the operating table 3. The surgeon 1 is performing the procedure using the laparoscopic tools 4 and 5 the robotic camera holder 100 is attached to the operating table rails 6 and positioned near the surgeon, holding the endoscope 7 that is inserted to the body of the patient 2.

FIG. 2 shows the robotic camera holder 300 attached to the operating table 3. The RCH is inserted to the adapter 10, which is connected to rails 6. the components of the RCH are shown: motor box 110, power transmission system 120 the robotic arm 1100 and the robotic arm housing 200 the endoscope 7 is inserted to the patient body 2 the camera 8 is attached to the distal end of the endoscope 7.

The endoscope is inserted through a tiny incision in the patient body.

In a free state the endoscope 7, as a rigid body, has 6 degrees of freedom.

The incision eliminates 2 DF of the endoscope by not allowing one end of the endoscope to move in 2 main directions. In order to have a fully defined position of the endoscope a mechanism with 4 degrees of freedom is needed.

FIG. 3 presents the 5 degrees of freedom of the robotic arm.

DF1 presents the ability of the robot to move the endoscope 8 to the right and left with respect to the robotic mechanism housing. 200

DF2 presents the ability of the robot to move the endoscope forward and backward with respect to the robotic mechanism housing.

DF3 presents the ability of the robot to move the endoscope in a zoom movement, i.e in and out of the patient body through the penetration point.

DF4 presents the ability of the robot to rotate the endoscope about its long axis. This degree of freedom is necessary when using endoscope with "angled" edge.

DF5 presents the ability of the robot to rotate the camera 8 with respect to the endoscope's long axis. This degree of freedom is necessary to keep the horizon of the image when using endoscope with "angled edge.

FIG. 4 shows the robotic mechanism 1000 locked in robotic mechanism housing 200. the RCH 1000 consist of two main components: the robotic arm that moves the endoscope in the direction of DF1 and DF2. Component 1200 moves the endoscope in the direction of DF 3 DF4 and DF5.

The robotic arm 1100 will be described in details at FIGS. 5a, 5b, 5c.

Figure 5A:
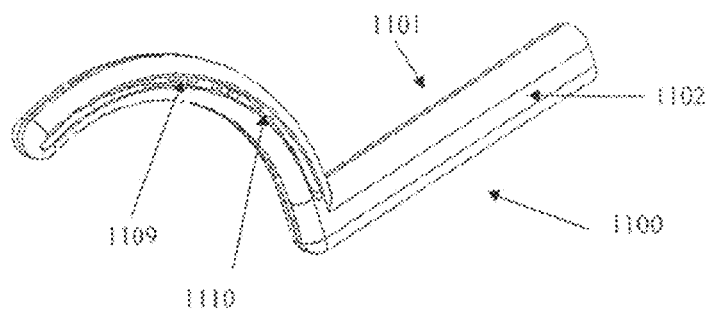
FIG. 5a shows the main parts of the robotic arm.

FIG. 5a shows the main parts of the robotic arm 1100. The body of the robotic arm consists of two arced shape elements 1101 and 1102. the robotic arm moves in the direction of DF1, from side to side. The robotic arm includes an inside mechanism that moves a chain that pulls (backward) and pushes (forward) component 1200 in the direction of DF2. A part of this chain 1110 is shown partly through slot 1109.

Figure 5B:
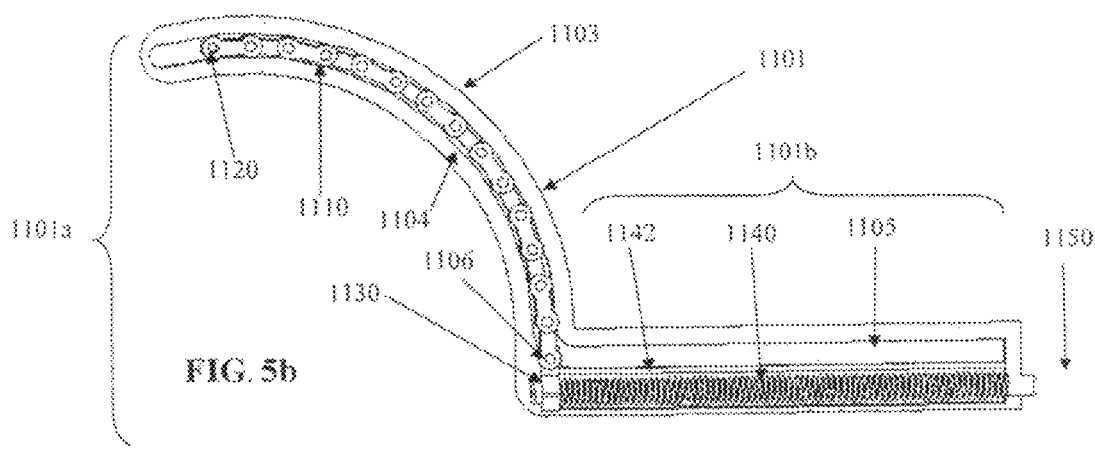
FIG. 5b shows the inside mechanism of the robotic arm.

FIG. 5b shows the inside mechanism of the robotic arm. In the arced shape 1101a of part 1101 the arced slot 1104 contains the chain 1110 that adapts it's shape to the curved slot 1104. the nut 1130 moves forward and backward according to the rotation of screw 1140 placed in slot 1142. The nut 1130 is connected to chain 1110 via pin 1106. When the nut moves backward it pulls chain 1110 into the linear slot 1105, performing the forward movement of DF2. When the nut moves forward it pushes chain 1110 out the linear slot 1105, performing the backward movement of DF2.

Component 1200 is attached to the robotic through a connecting pin placed in hole 1120 at the first link of the chain.

Figure 5C:
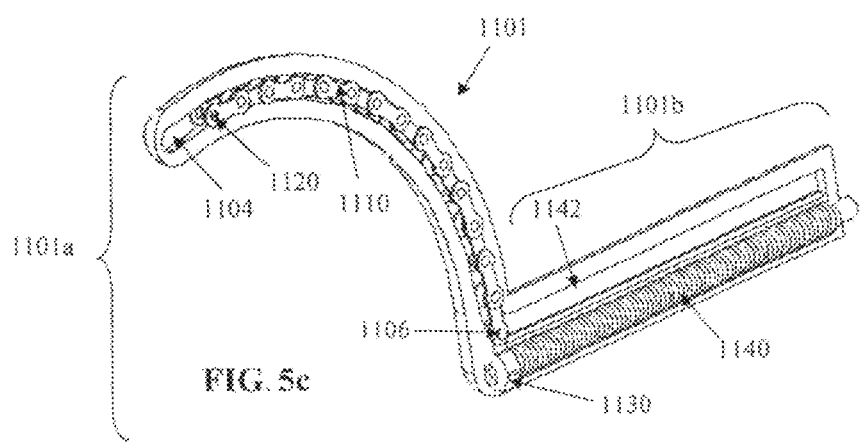
FIG. 5c shows in perspective view the inside mechanism of the robotic arm.

FIG. 5c shows in perspective view the inside mechanism of the robotic arm.

Figure 6:
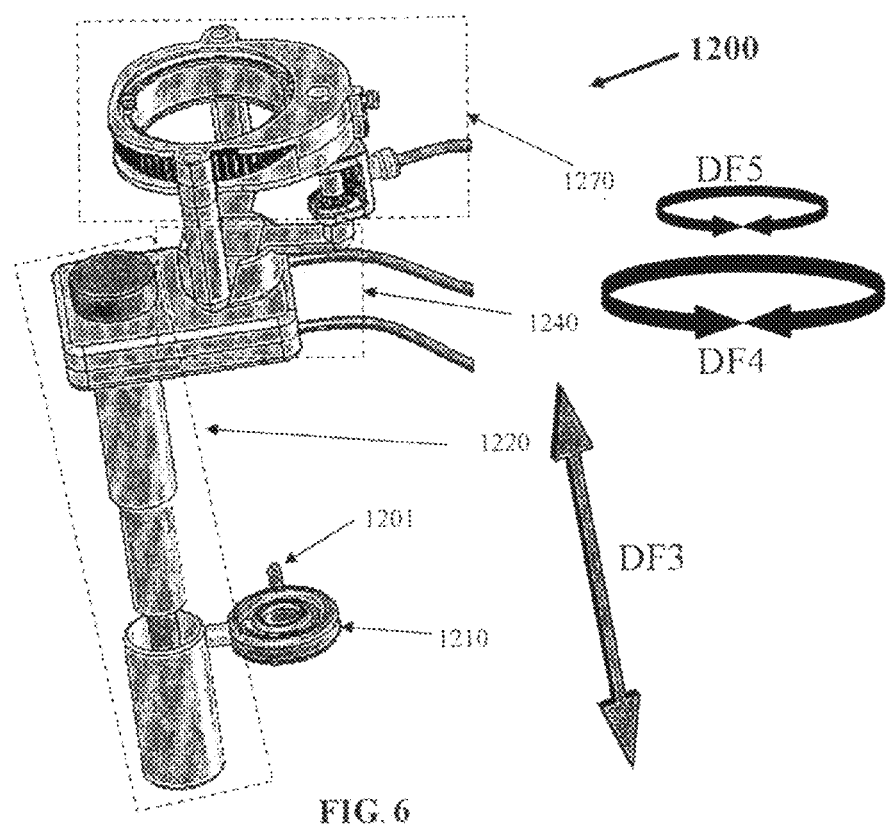
FIG. 6 shows in perspective view the The DF 3, 4, 5 components.

FIG. 6 shows in perspective view the The DF3,4,5 component 1200. component 1200 moves the endoscope in a linear motion DF3 1220, and two rotation movement: DF4 that rotates the endoscope about the endoscope's long axis. This movement is done by mechanism 1240 and DF5 that rotates the camera with respect to the endoscope's long axis, by mechanism 1270. Component 1200 is connected to the robot arm 1100 via pin 1201.

Figure 7:
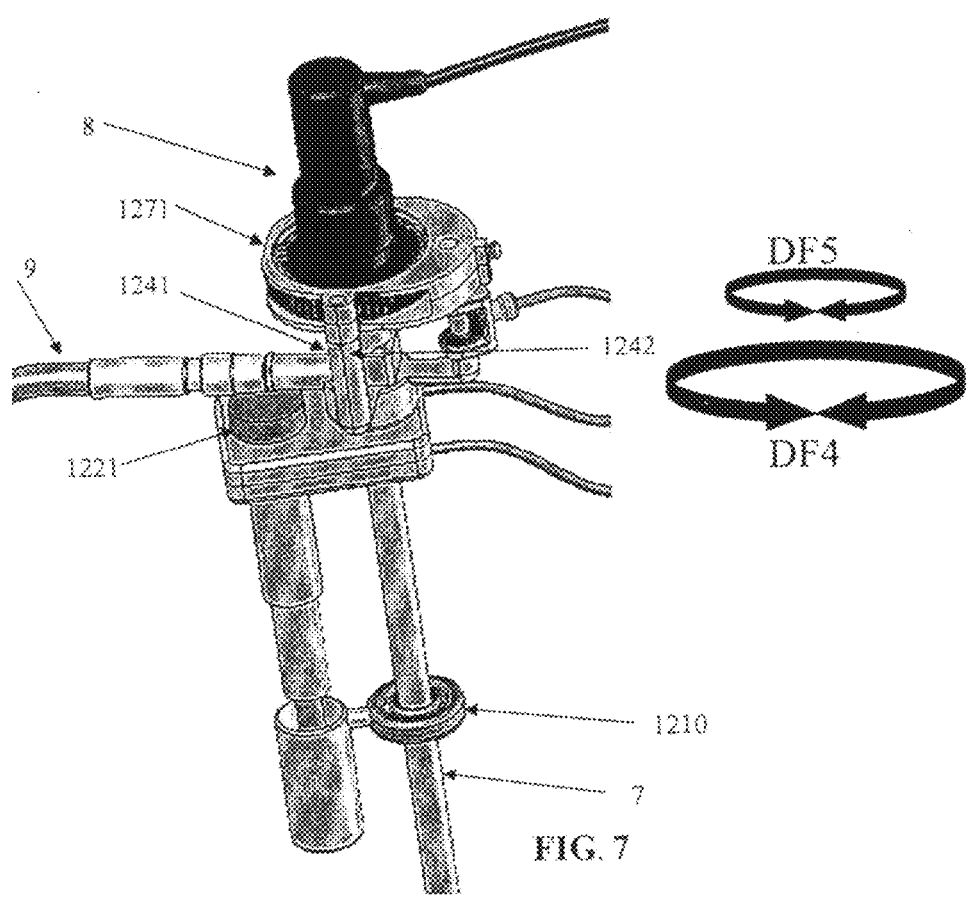
FIG. 7 shows in perspective view the endoscope 7 held by component 1200.

FIG. 7 shows in perspective view the endoscope 7 held by component 1200. and the relations between the different degrees of freedom of the mechanisms. The endoscope 7 is held by housing 1241 that rotates in the direction of DF4 and the camera 8 is held by housing 1271 that moves in the direction of DF5. these independent motions enables the control of angled endoscope to achieve a desired view for the surgeon, while maintaining the horizon position when rotating the camera 8 in the direction of DF5. The optic fibers cable 9 that transmits the light to the optic fibres of the endoscope, is shown with relation to the top part 1221 of the zoom component 1220, demonstrating the ability of the endoscope 7, to rotate, if needed a complete circle with no interference. The endoscope passes through the gimbal 1210 into the trocar (not shown)

FIG. 8a shows the zoom mechanism and parts. The zoom mechanism in principle consists of chain of screws. One of the screws is fixed with respect to the other screws. The other screws serve also as a nut. All screws have the same pitch, so any of the screws that are being screwed, do not change the rate of change of the height of the zoom.

A typical screw 1223 is shown in FIG. 8c the screw as a outer thread 1223a and a inner thread 1223b.

FIG. 8d shows part of the zoom mechanism. The fixed screw 1224 that has only outer thread is shown screwed in the inner thread of screw 1223a.

FIG. 8e shows the worm gear that transmits the rotation to the screws of the gear mechanism. When shat 1261 is being rotated the cylinder of the worm gear rotates and rotates gear 1263 that is coupled to the head of crew 1221 the rotation movement of screw 1221 rotates one or more screws in the chain, the zoom height changes according to the screw 1263 direction of rotation.

FIG. 8b shows the zoom in almost its lowest position. The screws are contained in cylinder 1225 cylinder 1225 is connected to gimbal 1210 via pin 1226 that does not allow cylinder 1225 to move or rotate. Cylinder 1225 serves also as the fixed point for screw 1224 that is connected rigidly to it's center.

FIGS. 9a and 9b show the mechanism that rotates endoscope 7 in the direction of DF4. The gear that rotates the endoscope is located in gearbox 1260 shown in FIG. 9a. The worm gear 1265 located on shaft 1264 transmits the rotation to the gear 1266. The endoscope 7 passes through hole 1266a and rotates with the gear 1266 as will be explained in FIG. 9b.

FIG. 9b shows the endoscope housing 1270 housing 1240 has three arms 1240a,b,c that hold the mechanism that moves camera 8 in the direction of DF5. the arms 1240 arises from structure 1241 that contains in the squared hole 1241a the head 7a of the endoscope, and in semi circular hole 1241b the endoscope's optic fiber connection 7b. the quick release extension 1241c is inserted into gear 1266 and the pin 1241d (not shown) located at the bottom of housing 1241 is inserted into hole 1266a forcing housing 1241 to rotate together with gear 1266.

The pin and hole structure is used to keep the orientation of the endoscope when the endoscope is re inserted after it was pulled out of the mechanism.

Figures 10A, 10B:
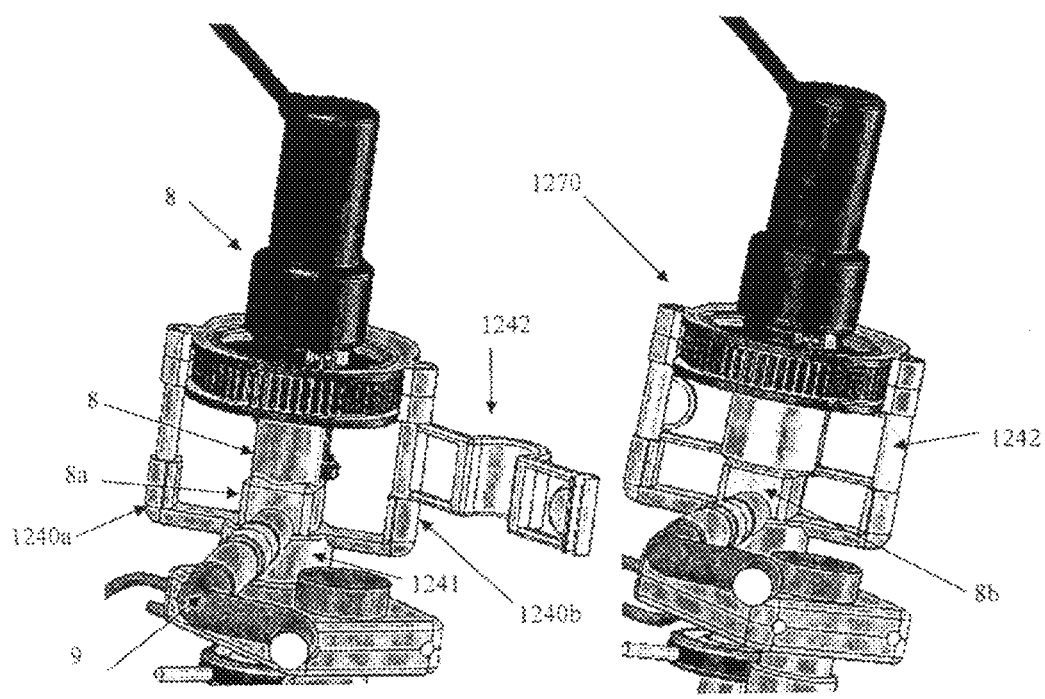
FIGS. 10a-10c show a lock mechanism that holds the endoscope from being pulled out from its position.
Figure 10C:
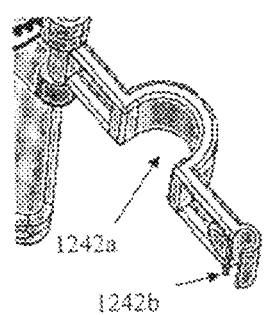

FIGS. 10a-10c show a lock mechanism that holds the endoscope from being pulled out from it's position. The locker arm 1242 is connected to arm 1240b and rotates freely about it. In order to lock the endoscope in its position the locker arm is rotated to the position shown in FIG. 10b. In order to keep the locker arm in its place, the locker arm has notch 1242b in it's free side. Also the locker arm has a curved part 1242a that fits the endoscope body.

FIG. 11a to FIG. 11f shows the mechanism 1270 that moves the camera head 8 in the direction of DF5 the mechanism 1270 is adopted on the top mechanism 1240: arms 1240a and 1240b passes through holes in arms 1277a and 1277b.

FIG. 11a show a general perspective view of the main parts of mechanism 1270. Housing 1271 contains gear 1273 that rotates camera head 8. Camera head 8 is fixed in gear 1273 by adapting ring 1272. As shown in FIG. 11c, adapting ring 1272 is a split so it can be fitted to various sizes of camera heads. In order to insure a tight fixation of ring 1272 to camera head 8, screw 1275 is used as shown in FIG. 11b. FIG. 11c also shows the pin 1276a arises from ring 1272. When fixing camera head 8 into gear 1273 pin 1276a is fixed in notch 1276b shown in FIG. 11d. This mechanism insures that camera head 8 will move together with gear 1273 with out any slip. Another task of this mechanism, when removing the endoscope with camera head (in order to clean the endoscope for example) is to maintain the orientation of camera head 8 with respect to gear 1273 when fixing the endoscope back to it's position.

FIG. 11e shows the gear transmission of mechanism 1270. Axis 1277b arises from arm 1240c (shown in FIG. 9b.) is connected to gear 1282 and gear 1285. the gear house 1280 contains vertical gear 1283. when the vertical gear 1283 is rotated by axis 1281, it transmit the rotation through gear 1283 and gear 1285 to gear 1273 and to the adapting ring 1272 which holds the endoscope and rotates it.

FIG. 11f shows the two independent degrees of freedom DF4 and DF5. The orientation of the camera (shown in white doted line) is different from the orientation of the endoscope (shown in black doted line).

Figure 12:
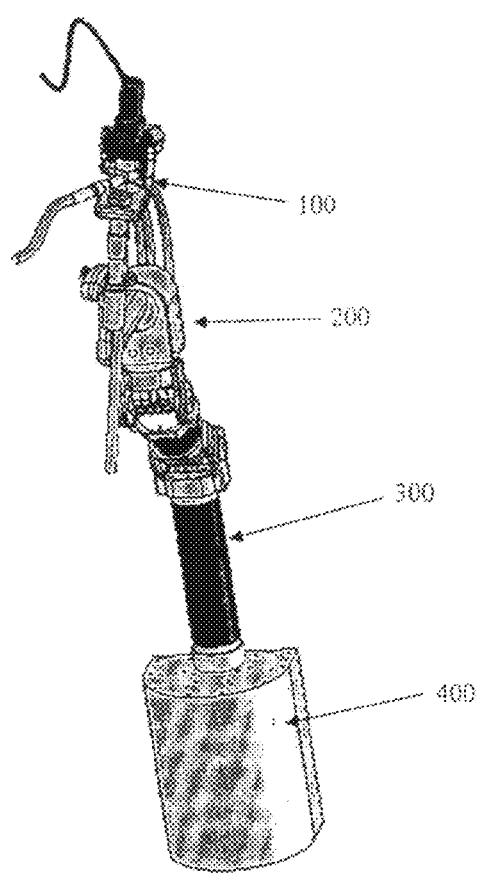
FIG. 12 shows the main components of the robot.

FIG. 12 shows the main components of the robot: component 100 is the robot arm mechanism that holds the robot and moves it in the direction of it's five independent degrees of freedom. components 200,300,400 creates the power that drives the robotic arm mechanism.

Component 400 includes the motors that produce the driving power.

Component 300 is a contraction that transfers the motor power to the part 200.

Component 200 is a gear box that transfers the direction of the rotation axis, while changing the transmission ratio. Component 200 serves also as the housing of component 100.

Figure 13:
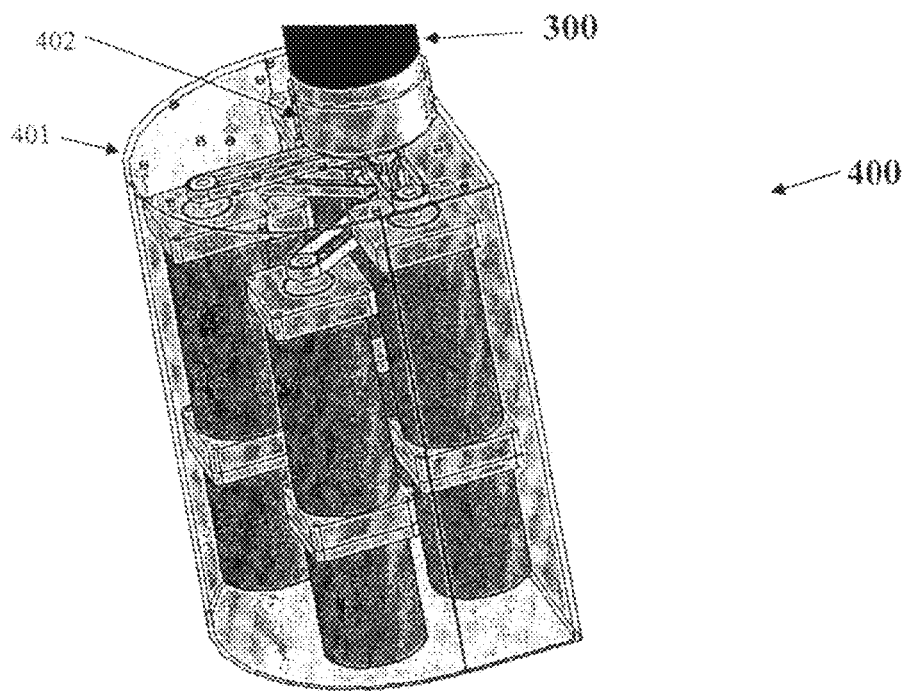
FIG. 13 shows the motors box.

FIG. 13 shows component 400 of the system in details. Component 400 includes motors box 401 with adaptor 402 that connects component to component 300.

The driving system (motors, gears Etc.) is fixed to the motor box.

Figure 14:
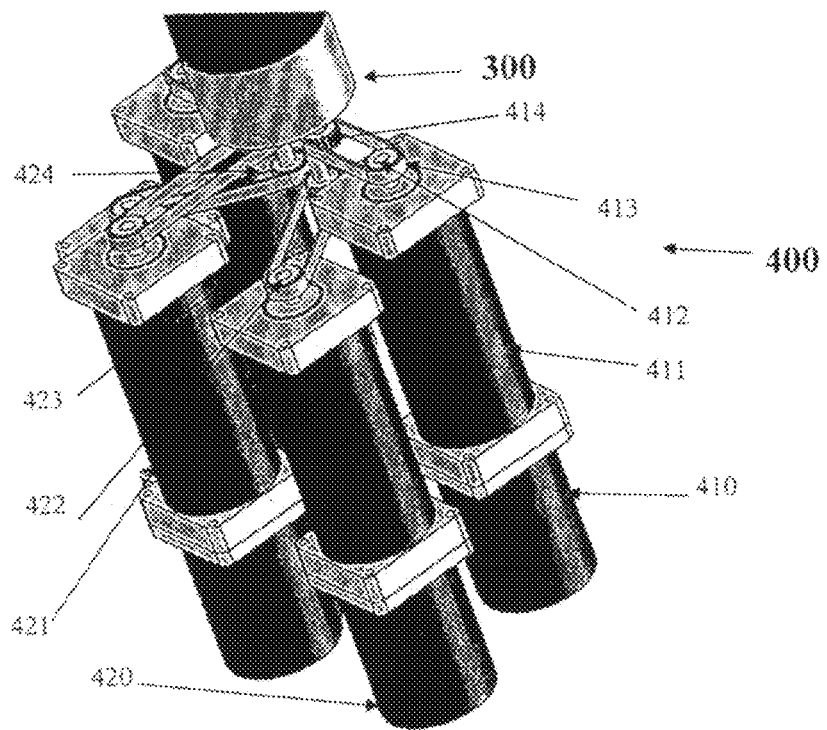
FIG. 14 shows the driving system setup.

FIG. 14 shows the driving system setup. The driving system includes motors, gear transmissions attached to the motors and transmission means that connects the motors' gear boxes to the shafts in that drive the motors' power through component 300.

A simple setup includes motor such as 410, 420, gearbox attached to the motor 411,421, gear mountained on the output shaft of the gear box 412,422, transmission means to component 300 shaft, seen here as belts 413 and 414. Belts 413 and 423 transmits power to gears 414 and 424 fixed to component's 300 shafts.

Of course there may other ways of designing another kinds of small effective motor box with the same performance.

Figure 15:
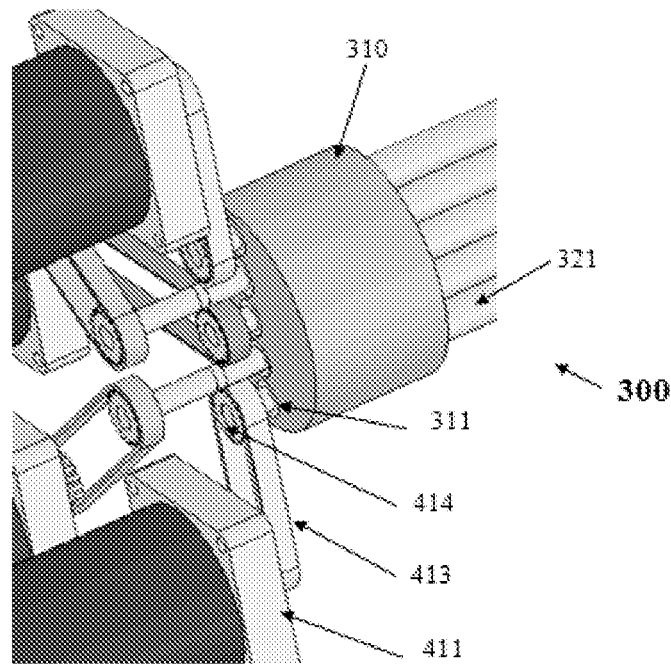
FIG. 15 show another view of connection between the motor gear and the shaft.

FIG. 15 show another view of connection between the motor gear 411 and the shaft 311. while belt 413 rotates it rotates also gear 14 that is fixed to shaft 311.

FIG. 16 *a* shows the power transmission system 300. The power transmission system consists of pipe structure that connect the motor box 400 to the robotic arm 200.

The lower pipe 320 is vertical an is connected to pipe 300 by joint 350. pipe 300 may be positioned in various angles with respect to the vertical pipe 320. another joint 360 may be used for positioning the upper part of the joint 365, which is connected to the robotic arm housing 200. Joint 350 and 360 angle are changed by rotating screws 351 and 361 respectively. The power produced in the motor box is transmitted to the robotic arm by shafts placed in the pipes. In order to be able to bend the joints of the pipe structure a cardan joints (354 and 364 for example) are used. Flexible shafts may be used also to transmit the motors rotation to housing 200.

FIG. 16 *b*. shows the power transmission system 300. Pipes 320 and 330 are shown in transparent, shaft 321 and shaft 331 may be seen.

Figure 16A:
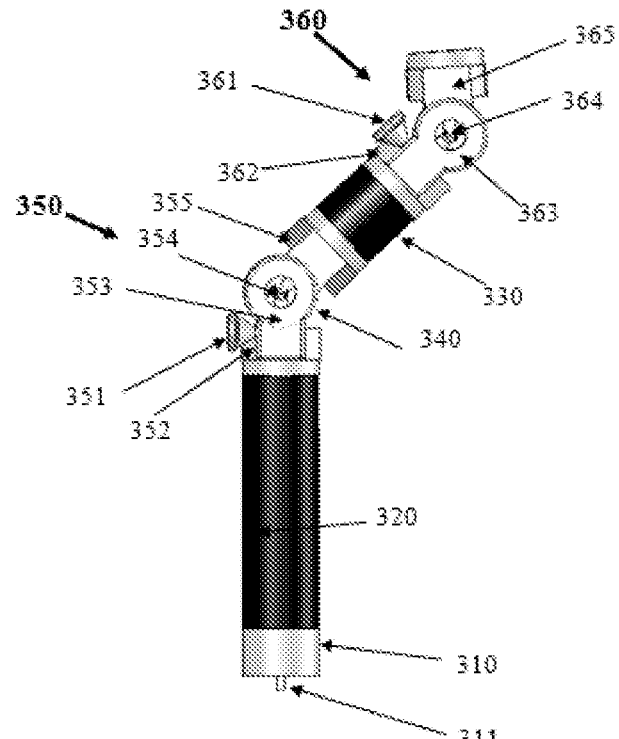
FIGS. 16a-16e show the power transmission system.
Figure 16B:
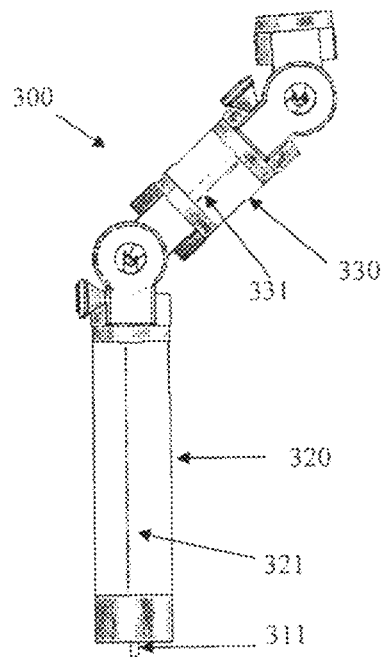
Figure 16C:
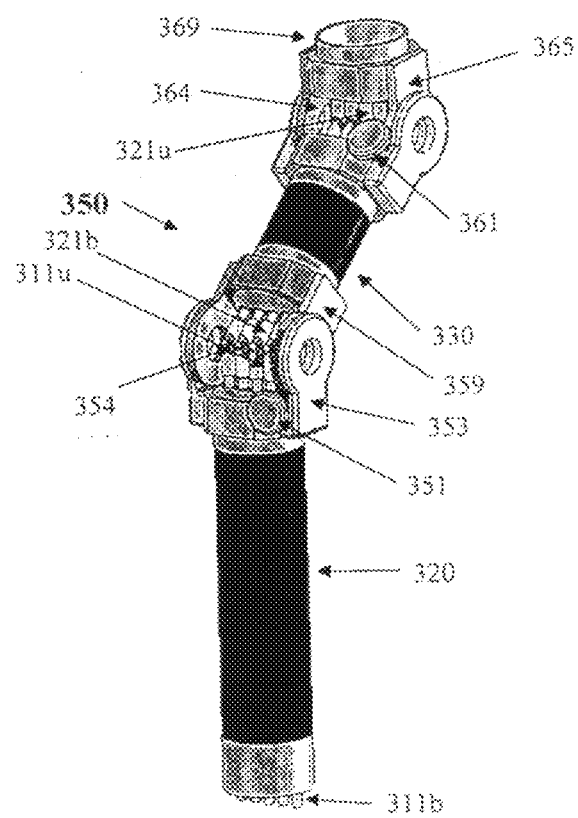

FIG. 16*c* shows power transmission system 300 in perspective view. In order to simplify the explanation will refer to only one shaft. The bottom end of shaft 311 arises from the bottom of pipe 320. The upper end of shaft 311*u* is connected to the next shaft bottom 321*b*, with a Cardan joint 354. Shaft 321 upper end 321*u*, is connected to Cardan joint 364 transmitting the motor rotation into the upper end 359 of joint 360.

Figure 16D:
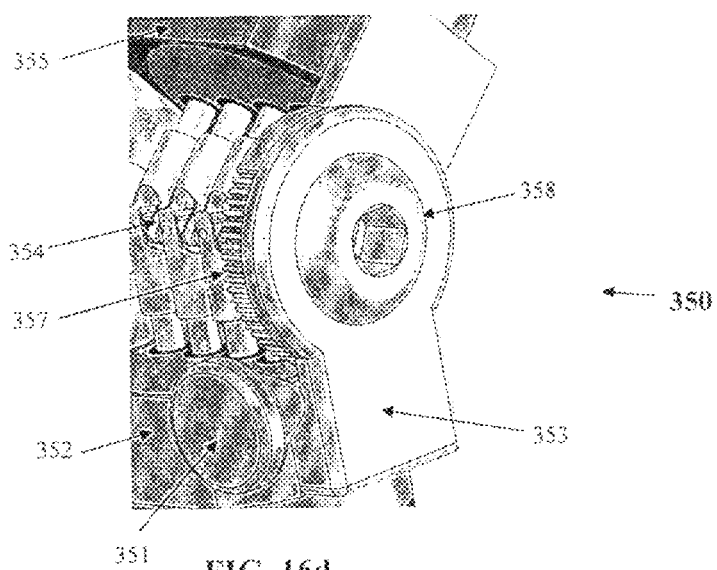

FIG. 16*d* shows in details the structure of joint 350. Joint 350 allows the surgeon to position the robotic camera arm in a favor position, without interfering the transmission of power from motor box 400 to the arm housing 200. Arm 355*a* is connected rigidly to housing 355. Arm 353 is connected rigidly to housing 352. Arm 353 and 355*a* are connected with pivot 358. Cardans 354 with their axis aligned with the center of pivot 358, allowing the joint to bend freely. The surgeon may bend the joint by rotating the screw 351

Figure 16E:
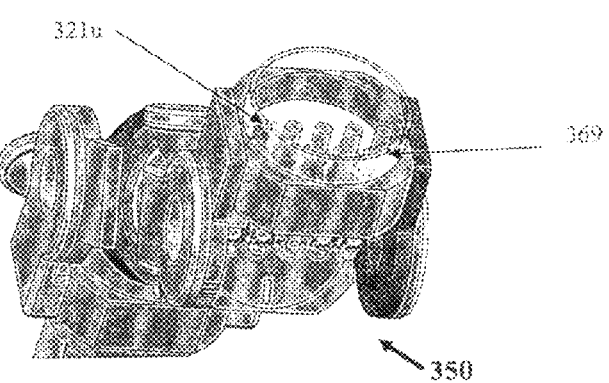

FIG. 16*e* shows another view of joint 350. The upper side 369 is shown in transparent and the upper part 321*u* of shaft 321 is shown.

Figure 17:
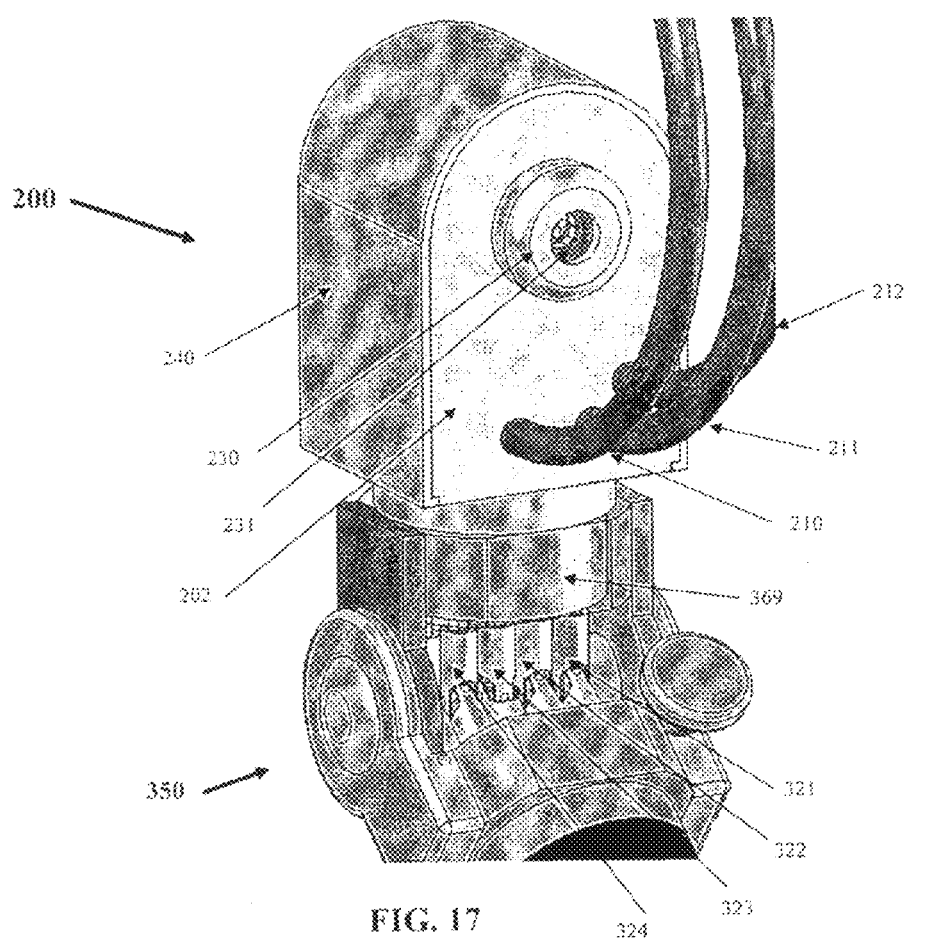
FIG. 17 shows the robotic arm housing.

FIG. 17 shows the robotic arm housing 200. Housing 200 is attached on top of joint 350 in adapter 369 that contains the ends of shafts 321, 322, 323 etc. housing 200 has a cover 240.

Tubes 210, 211, 212 are rising from the back of housing 200. As will be described later these tubes contain flexible shafts that transmit rotation movement to component 1200 of the robotic arm 1000. The back of housing 200 contains also adapter 230 that holds shaft 1150 of component 1100 of robotic arm 1000. Shaft 1150 is secured in hole 231.

Figure 18:
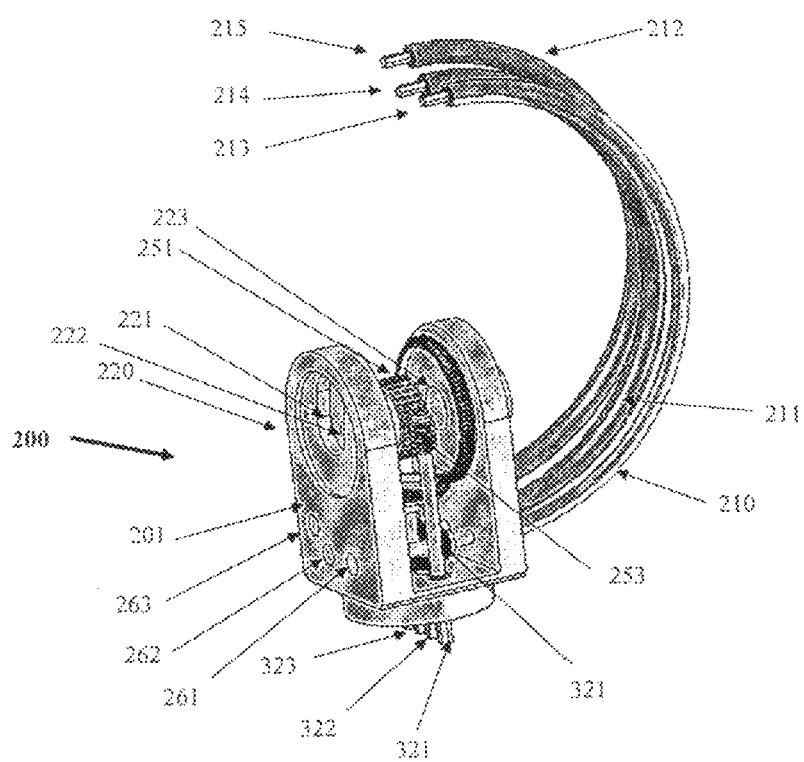
FIG. 18 shows the gear housing in front view with it's cover removed exposing the gears that transmits the motors to the robotic different arm mechanisms.

FIG. 18 shows housing 200 in front view with cover 240 removed exposing the gears that transmits the motors to the robotic different arm mechanisms. In the front 201 of housing 200, cylinder 220 with recess 221 is seen. Cylinder 220 rotates the robotic arm 1100 in direction of DF1. The back of robotic arm 1100 is secured into recess 221 and shaft 1150 pass through holes 222 and 223 to the back 202 of housing 200. Shaft 321 rotates worm gear 253 that rotates gear 251 that rotates cylinder 220. Shafts 322 and 323 and 324 (not seen) transmits their rotation, as will be described later, to shafts 261, 262 and 263. Shafts 261, 262 and 263 rotate the flexible shafts 213, 214 and 215 respectively. The ends of flexible shafts arises from flexible tubes 210, 211 and 212.

Figure 19:
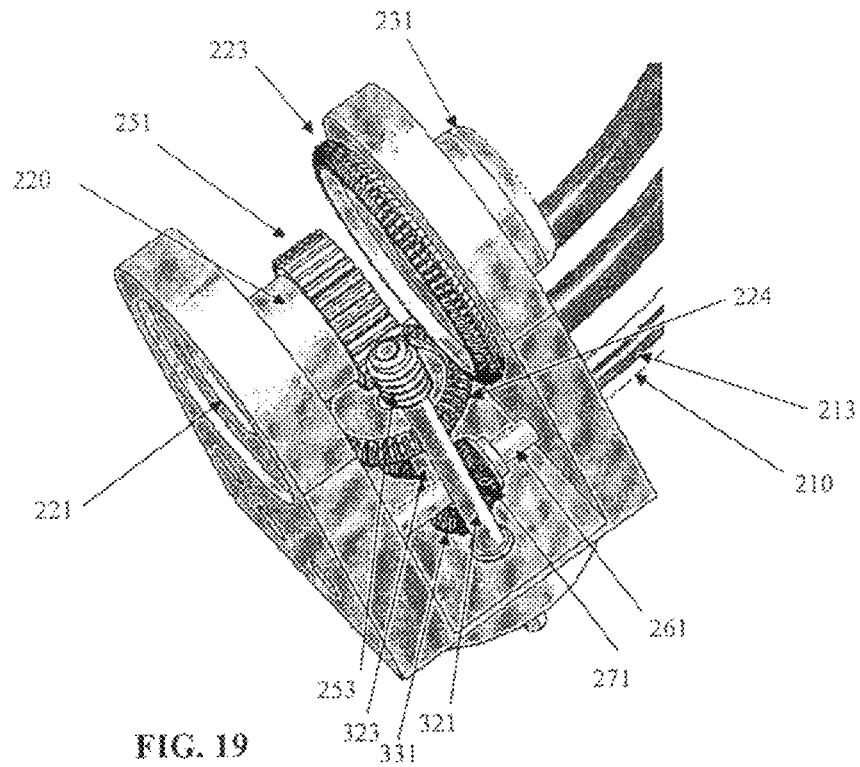
FIG. 19 shows in closer view the mechanisms in housing.

FIG. 19 shows in closer view the mechanisms in housing 200. The rotation of the robotic arm from side to side, in the direction of DF1 is achieved by rotating gear 251 by worm 253 attached to vertical shaft 321. The rotation of screw 1140 that enables the movement of the endoscope forward and backward in respect to the robotic arm is achieved by restating gear 223 by vertical gear 224 which is attached to shaft 323. Gear 223 rotates screw 1140 via clutch located in housing 231.

The principle of the transmission of the rotation to the flexible shafts remains the same for all of the flexible shafts: the horizontal gear 331 rotates vertical gear 271. Gear 271 is attached to shaft 261. Shaft 261 is connected to flexible shaft 213 which is located in flexible tube 210 that directs flexible shaft 213 upward to it's connection with mechanism 1000.

Figure 20:
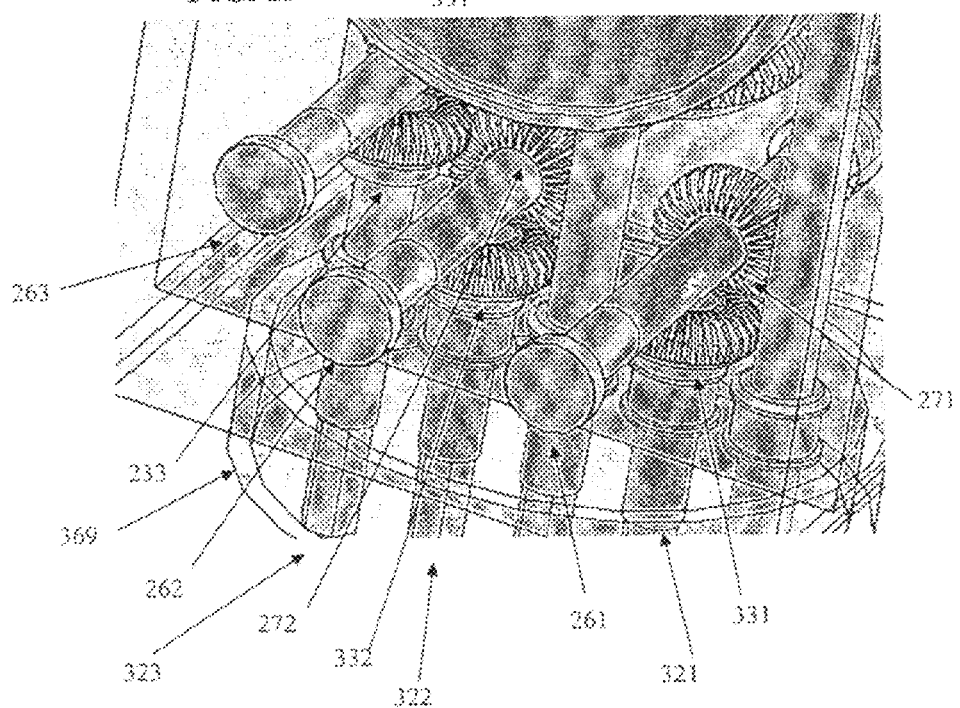
FIG. 20 shows from another angle the inner mechanism of housing.

FIG. 20 shows from another angle the inner mechanism of housing 200.

Housing 200 is shown in transparent and the gear transmission between the horizontal gears 331, 332 and 333 and the vertical gears 272, 272 and 273 respectively is demonstrated. The ends of shafts 321, 322 and 323 are shown. This structure enables quick disassembling for simple maintenance and to use different kinds of housings for that activates different robotic mechanisms with the same motors no need to release from the operating table, the other main parts of the robotic system.

Figure 21:
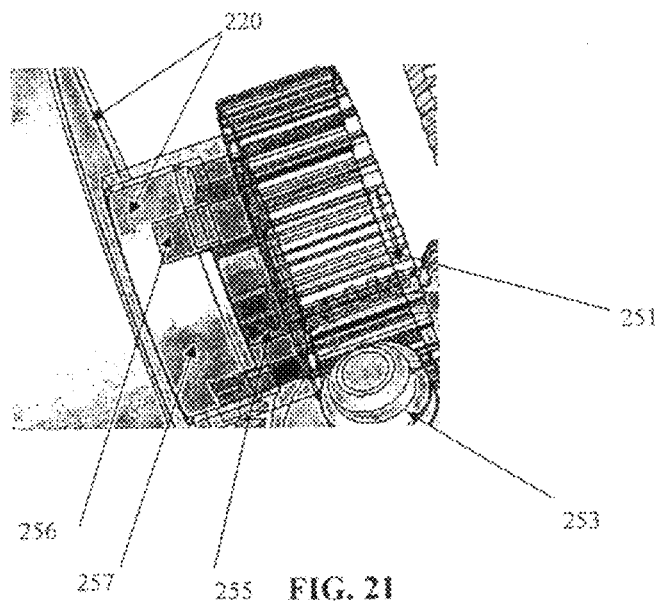
FIG. 21 shows the clutch mechanism that may protect the patient body from being hurt.

FIG. 21 shows the clutch mechanism that may protect the patient body from being hurt by an allowed forces applied by the robotic arm. In this example the clutch consists of two magnets 256 and 257 that attached to each other by their magnetic force. Magnet 256 is attached rigidly to gear 251 and magnet 256 is attached rigidly to the robotic arm housing 220. While rotating the robotic arm in the direction of DF1, if the force applied by the endoscope on the patient body exceeds a threshold level, the magnets slides on each other and the robotic arm stops moving in the direction of DF1. The magnets may be changed in respect to nature of the surgery or to the patient properties: fat or thin patient, infant or adult.

Figure 22:
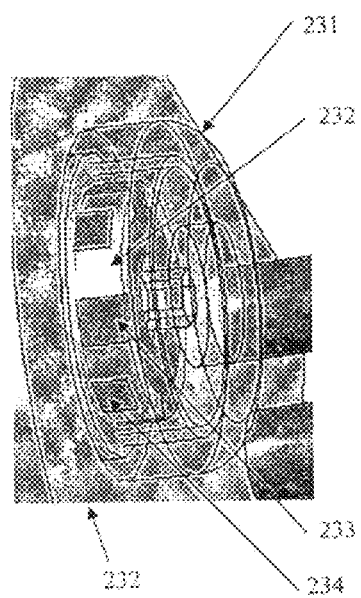
FIG. 22 shows the clutch mechanism that may protect the patient body from being hurt.

FIG. 22 shows the clutch mechanism that may protect the patient body from being hurt by an allowed forces applied by the robotic arm. In this example the clutch consists of two magnets 233 and 234 that attached to each other by their magnetic force. Magnet 234 is attached rigidly to gear 223 (not shown) and magnet 233 is attached rigidly to the robotic screw 1140 (not shown). While moving the endoscope forward and backward in the direction of DF2, if the force applied by the endoscope on the patient body exceeds a threshold level, the magnets slides on each other and the endoscope movement in the direction of DF1 stops. The magnets may be changed in respect to nature of the surgery or to the patient properties: fat or thin patient, infant or adult.

Figure 23A:
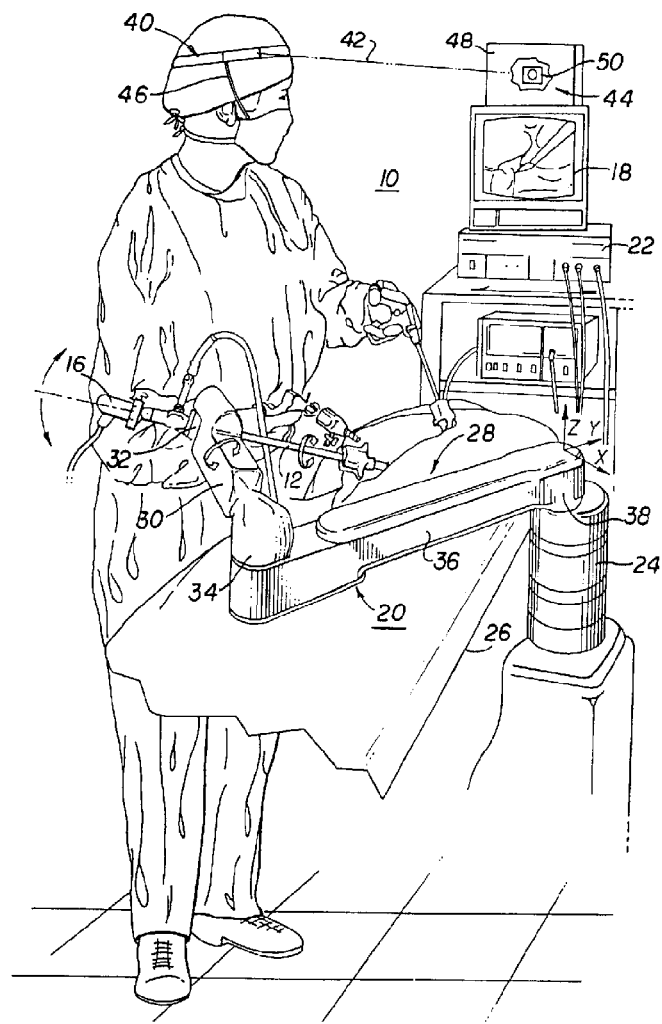
FIGS. 23a, 23b, 23c show prior art patents.
Figure 23B:
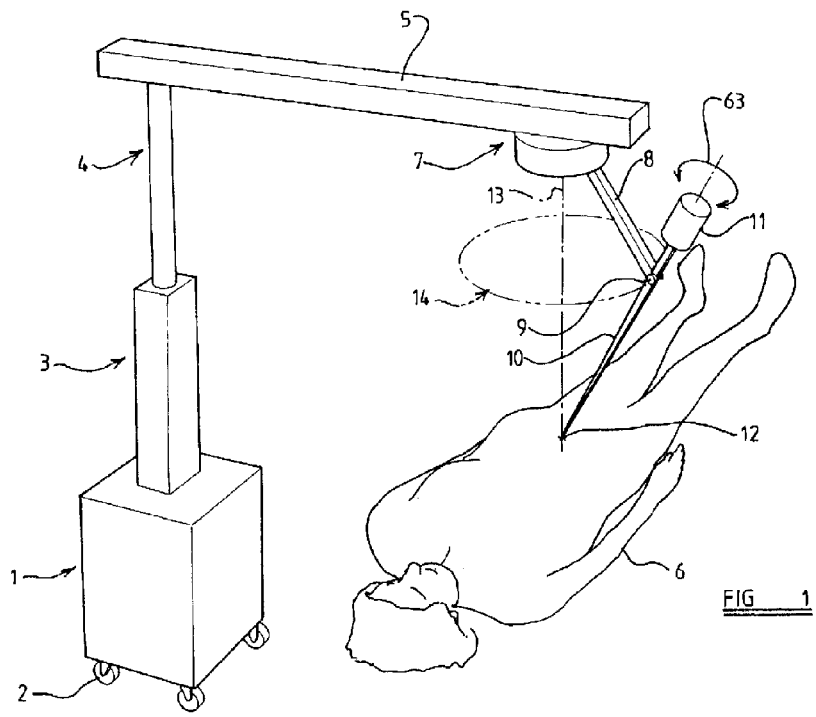
Figure 23C:
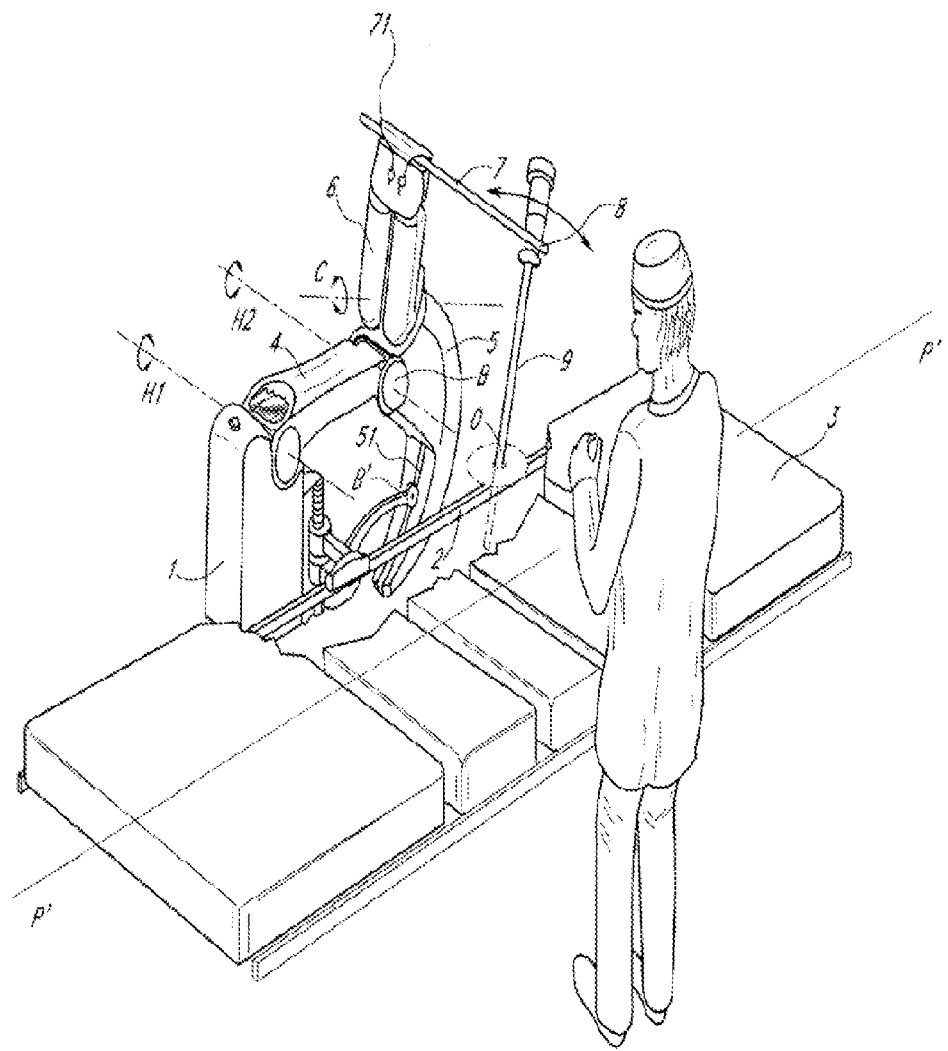

FIGS. 23*a*, 23*b*, 23*c* shows prior art patents

What is claimed is:
1. A surgical instrument handling system, useful for observation and/or intervention with respect to a patient's body; said surgical instrument handling system comprising:
   a fixed support;
   a hinge that enables changing an inclination of said surgical instrument handling system;
   a flexible power transmission system;

a gear housing adapted to change a direction of rotation of motors-transmitted by said flexible power transmission system;

a camera housing adapted to house a camera;

a surgical instrument handling mechanism, said surgical instrument handling mechanism comprising:

a first small size moveable element, connected to the gear housing, adapted to maneuver a second moveable element simultaneously in at least one of four main directions selected from right, left, forward and backward; and, a third moveable element adapted to move said surgical instrument in directions selected from zoom in and zoom out, rotation of said surgical instrument, either clockwise or counter-clockwise; and, an actuator system that produces a rotational movement utilized by said surgical instrument handling mechanism;

wherein said surgical instrument handling system further enables clockwise and counter clockwise rotation of said camera housing with respect to said surgical instrument.

2. The surgical instrument handling system according to claim 1, wherein the flexible power transmission system comprises a plurality of tubes interconnected via a plurality of joints, adapted to rotate to and to keep any desired angle.

3. The surgical instrument handling system according to claim 2, wherein said tubes contain shafts that transmit the actuators' rotation to said gear housing.

4. The surgical instrument handling system according to claim 1, wherein said gear housing comprises a plurality of gear transmissions that may move simultaneously the moveable parts of said surgical instrument handling mechanism.

5. The surgical instrument handling system according to claim 4, wherein said gear transmissions transfer power to said moveable parts of said first moveable element and said second moveable element via a clutches that stops said power transmission at a desired threshold.

6. The surgical instrument handling system according to claim 5, wherein said clutches allows a surgeon to move said surgical instrument without the need to disconnect said surgical instrument from said surgical instrument handling mechanism.

7. The surgical instrument handling system according to claim 1, wherein said first small size moveable element has a spatial structure, wherein said element contains a pushing and pulling mechanism to produce said forward and backward movement of said surgical instrument.

8. The surgical instrument handling system according to claim 1, wherein said first small size moveable element is connected to a gear transmission of said gear housing that rotates said first moveable element in said right and left directions.

9. The surgical instrument handling system according to claim 1, further comprising a gimbal connection between said first small size moveable element and said surgical instrument, thereby isolating said body of said patient from the surgical instrument handling mechanism.

10. The surgical instrument handling system according to claim 1, wherein said second moveable element comprises a linear connection to said first small size moveable element.

11. The surgical instrument handling system according to claim 1, wherein said second moveable element comprises a gear housing allowing transfer of rotational power by said flexible power transmission system to produce movements of said surgical instrument in desired directions.

12. The surgical instrument handling system according to claim 1, wherein said second moveable element comprises a gear housing allowing transfer of rotational power by said flexible power transmission system to produce either a linear movement or a rotational movement of said surgical instrument.

13. The surgical instrument handling system according to claim 1, wherein said second moveable element comprises a gear housing allowing transfer of rotational power by said flexible power transmission system to produce said rotational movement of said camera with respect to said surgical instrument.

14. The surgical instrument handling system according to claim 1, wherein said second moveable element comprises a quick release mechanism enabling fast removal and fast installation of said surgical instrument.

15. The surgical instrument handling system according to claim 1, wherein said second small size moveable element comprises an adapter allowing use of several surgical instruments.

16. The surgical instrument handling system according to claim 1, having a structure that has a small presence above and near said body of said patient, thereby preventing distraction of a surgeon.

17. The surgical instrument handling system of claim 1, wherein said handling surgical instrument mechanism has a structure and mechanism that may be manufactured from inexpensive materials.

* * * * *